US010864200B2

(12) United States Patent
Hegel et al.

(10) Patent No.: US 10,864,200 B2
(45) Date of Patent: Dec. 15, 2020

(54) STABLE FORMULATIONS FOR IMMUNE-MODULATORY MACROLIDES

(71) Applicant: Roche Diagnostics Operations, Inc., Indianapolis, IN (US)

(72) Inventors: Ewelina Hegel, Mannheim (DE); Hans-Peter Josel, Weilheim (DE); Eloisa Lopez-Calle, Ludwigshafen (DE); Josef Roedl, Mutterstadt (DE); Noah Weiss, Cypress, TX (US); Benjamin Tiemann, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/562,629

(22) Filed: Sep. 6, 2019

(65) Prior Publication Data
US 2019/0388402 A1 Dec. 26, 2019

Related U.S. Application Data

(63) Continuation of application No. PCT/EP2018/055465, filed on Mar. 6, 2018.

(30) Foreign Application Priority Data

Mar. 7, 2017 (EP) .................................... 17159619

(51) Int. Cl.
*A61K 31/436* (2006.01)
*A61K 9/08* (2006.01)
*A61K 47/18* (2017.01)

(52) U.S. Cl.
CPC .............. *A61K 31/436* (2013.01); *A61K 9/08* (2013.01); *A61K 47/18* (2013.01)

(58) Field of Classification Search
CPC ......... A61K 31/436; A61K 9/08; A61K 47/18
See application file for complete search history.

(56) References Cited

FOREIGN PATENT DOCUMENTS

| EP | 0878714 A1 | 11/1998 |
| EP | 2003455 A1 | 12/2008 |
| EP | 2402350 A1 | 1/2012 |

OTHER PUBLICATIONS

Riss et al. Cell Viability Assays. 2013,pp. 1-25. In: Assay Guidance Manual. Sittampalam et al., editors. Eli Lilly & Company and the NCATS, Bethesda MD. (Year: 2013).*
Baldelli, Sara et al., High-performance liquid chromatography with ultraviolet detection for therapeutic drug monitoring of everolimus, Journal of Chromatography B, 2005, pp. 99-105, vol. 816.
Capone, D. et al., Stability of Sirolimus and Everolimus Measured by Immunoassay Techniques in Whole Blood Samples from Kidney Transplant Patients, International Journal of Immunopathology and Pharmacology, 2008, pp. 297-307, vol. 21, No. 2.
Freeman, David J. et al., Stability of FK506 in Whole Blood Samples, Therapeutic Drug Monitoring, 1995, pp. 266-267, vol. 17, No. 3.
Ingels, Stephen C. et al., Stability of FK506 (Tacrolimus) in Whole-Blood Specimens, Clinical Chemistry, 1995, pp. 1320-1321, vol. 41, No. 9.
International Search Report dated May 22, 2018, in Application No. PCT/EP2018/055465, 3 pp.
Kaplan, Ibrahim et al., Effects of Storage Temperature and Time on Stability of Serum Tacrolimus and Cyclosporine A Levels in Whole Blood by LC-MS/MS, International Journal of Analytical Chemistry, 2015, 5 pp., Article ID 956389.
Khoschsorur, GholamAli, Simultaneous Measurement of Sirolimus and Everolimus in Whole Blood in HPLC with Ultraviolet Detection, Clinical Chemistry, 2005, pp. 1721-1724, vol. 51, No. 9.
Kiss, B. et al., Evaluation of Rapamycin Stability in Whole Blood by HPLC with Ultraviolet Detection, Farmacia, 2006, pp. 103-111, vol. LIV, No. 5.
McDonnell, Gerald and Russell, A. Denver, Antiseptics and Disinfectants: Activity, Action, and Resistance, Clinical Microbiology Reviews, 1999, pp. 147-179, vol. 12, No. 1.
Salm, Paul et al., Quantification and stability of everolimus (SDZ RAD) in human blood by high-performance liquid chromatography-electrospray tandem mass spectrometry, Journal of Chromatography B, 2002, pp. 283-290, vol. 772.
Salm, Paul et al., Stability of Sirolimus (Rapamycin) in Whole Blood, Therapeutic Drug Monitoring, 2000, pp. 423-426, vol. 22, No. 4.
Sharma, Vivek et al., Rheology of globular proteins: apparent yield stress, high shear rate viscosity and interfacial viscoelasticity of bovine serum albumin solutions, Soft Matter, 2011, pp. 5150-5160, vol. 7.
Streit, Frank et al., Sensitive and specific quantification of sirolimus (rapamycin) and its metabolites in blood of kidney graft recipients by HPLC/electrospray-mass spectrometry, Clinical Chemistry, 1996, pp. 1417-1425, vol. 42, No. 9.

(Continued)

*Primary Examiner* — Robert A Wax
*Assistant Examiner* — Olga V. Tcherkasskaya
(74) *Attorney, Agent, or Firm* — Stinson LLP

(57) ABSTRACT

The present description relates to a liquid composition having at least one immune-modulatory macrolide compound and an essentially cell-free blood hemolysate. The present description further relates to a method for manufacturing a stabilized immune-modulatory macrolide calibration solution, by a) preparing a solution comprising an essentially cell-free blood hemolysate, b) admixing a predetermined amount of at least one immune-modulatory macrolide into said solution comprising an essentially cell-free blood hemolysate, and, thereby c) manufacturing a stabilized immune-modulatory macrolide calibration solution. Furthermore, the present description relates to kits, uses, devices, methods and to an immune-modulatory macrolide compound calibration solution related thereto.

13 Claims, No Drawings

(56) References Cited

OTHER PUBLICATIONS

Upadhyay, Vivek et al., Liquid-liquid Extraction of Everolimus an Immunosuppressant from Human Whole Blood and its Sensitive Determination by UHPLC-MS/MS, Journal of Advancement in Medical and Life Sciences, 2014, 11 pp., vol. 1, Issue 3.

Yamashita, Kazunari et al., Establishment of new preparation method for solid dispersion formulation of tacrolimus, International Journal of Pharmaceutics, 2003, pp. 79-91, vol. 267.

\* cited by examiner

STABLE FORMULATIONS FOR IMMUNE-MODULATORY MACROLIDES

CROSS-REFERENCE TO RELATED APPLICATIONS

This application is a continuation of International Application No. PCT/EP2018/055465 filed Mar. 6, 2018, which claims priority to European Application No. 17159619.0 filed Mar. 7, 2017, the disclosures of which are hereby incorporated by reference in their entirety.

SUMMARY OF THE INVENTION

The present invention relates to a liquid composition comprising at least one immune-modulatory macrolide compound and an essentially cell-free blood hemolysate. The present invention further relates to a method for manufacturing a stabilized immune-modulatory macrolide calibration solution, comprising a) preparing a solution comprising an essentially cell-free blood hemolysate, b) admixing a predetermined amount of at least one immune-modulatory macrolide into said solution comprising an essentially cell-free blood hemolysate, and, thereby c) manufacturing a stabilized immune-modulatory macrolide calibration solution. Furthermore, the present invention relates to kits, uses, devices, methods and to an immune-modulatory macrolide compound calibration solution related thereto.

BACKGROUND OF THE INVENTION

Everolimus (Eve), sirolimus (Sir) and tacrolimus (Tac) are macrolide compounds which are used in medicine as immunosuppressive drugs (ISD) after organ transplant. These drugs have a narrow therapeutic range, where lower levels are associated with insufficient therapy and eventually lead to rejection of the organ, and on the other hand, where higher levels are associated with toxicity to certain organs like liver and kidney. In addition, intra- and inter-patient variability in pharmacokinetic and pharmacodynamics parameters complicates a balanced dosage of the ISD. Therefore, therapeutic drug monitoring (TDM) of these drugs has become an indispensable adjunct for the effective treatment of transplant patients by controlling the therapy based on concentrations in the body rather than by dose alone. Since everolimus, sirolimus and tacrolimus are highly bound to erythrocytes in the blood stream, the recommended matrix for the quantitation is whole blood.

For the determination of Eve, Sir and Tac in whole blood a broad range of TDM tests are commercially available, typically as immunoassays for automated analyzers, but also as LC-MS/MS (Liquid Chromatography with tandem mass spectrometry) tests. One important aspect for tests running on automated in vitro diagnostics (IVD) platforms is that all the required reagents, such as immunoreagents, controls, calibrators and internal standards in case of LC-MS/MS, are ideally provided as stable and ready-to-use solutions. These solutions can be placed on-board of the instrument for a longer period of time offering a workflow not needing user interactions. The use of reagents as lyophilisates is, however, necessary when chemically instable reagents are involved, but this hampers the workflow by requiring manual handling steps for reconstitution. Manual handling steps generate additional costs and also provide sources for errors. In addition, the reconstituted reagent typically shows short shelf-life and has to be replaced by freshly prepared solutions.

The typical solvent for assay reagents used for the immunochemistry-based IVD platforms is water. Reagents dissolved in aqueous-based solvents, i.e. buffers, ensure a full compatibility with the biomolecules involved in the assay, such as antibodies or other proteins, ensuring their intact 3-dimensional structure. Organic solvents, on the other hand, can cause, depending on their amount, a partial or total unfolding and deactivation of the biomolecules, thus disturbing the immunoassay. Also some of the LC-MS/MS methods for IVD need aqueous-based solutions for the pre-analytics and the reagents (e.g. internal standards for the MS method with enrichment workflow as taught in EP 2 003 455 A1). In the LC-MS/MS pre-analytics the samples (serum-, plasma- or whole blood) are treated with a release reagent in cases where a release of the analyte and/or removal of matrix components is necessary.

However, in contrast to solutions in organic solvents (e.g. methanol, acetonitrile), aqueous formulations of Eve, Sir and Tac are typically not stable for longer periods of time at storage temperatures which are used in lab refrigerators (2-8° C.) and on-board of analyzers (4-12° C.). It is known from literature (e.g. EP 2 402 350 A1) that the macrolides Eve, Sir and Tac have poor aqueous solubility and are unstable in solution as a consequence of solvolysis of their ester linkage, leading to a loss of biological activity. Thus, aqueous formulations of Eve, Sir and Tac, which are free of organic solvents, including blood-based samples, are typically stored at very low temperatures ranging from −20 to −80° C. in order to keep them stable and usable in IVD for longer periods of time; otherwise the solutions are only stable for a short time period (1-6 weeks at 2-8° C.). The prior art recommendations for storage are summarized in Table 1.

Table 1: Literature-provided stability of blood samples containing everolimus, sirolimus and tacrolimus (h: hour, d: day, w: week, m: month, a: year, RT: room temperature, Literature referred to as indexes is: (1) Capone et al. (2007), Int J. Immunopath Pharmacol 21(2):297; (2) Streit et al. (1996), Clin Chem 42:9, (3) Kiss et al. (2006), Farmacia Vol. LIV, 5: 103; (4) Salm et al. (2002) J Chromatogr B 772:283; (5) Salm et al. (2000), Ther Drug Monit 22(4):423; (6) Baldelli et al. (2005), J Chromatogr B 816:99; (7) Ingels et al. (1995), Clin Chem 41(9):1320; (8) Freeman et al. (1995), Ther Drug Monit 17(3):266; (9) Kaplan et al. (2015, Int J Anal Chem, Article ID 956389; doi:10.1155/2015/956389; (10) Upadhyay et al. (2014), J Adv Med Life Sci 1(3):1; (11) Khoschsorur (2005), Clin Chem 51(9):1721).

| Temperature | everolimus | sirolimus | tacrolimus |
| --- | --- | --- | --- |
| >RT | 7d/30° C. (in light) [1] | 8d/30° C. (dark & in light) [5] <br> 7d/30° C. (in light) [1] | 3d/37° C. [7] |
| RT | 1d/RT [11] <br> 15h/RT [6] <br> 8h/RT [10] <br> 6h/RT (in light) [4] | 1d/RT [11] <br> 1d/RT [3] | 14d/RT [8] <br> 7d/RT [7] <br> 1d/RT not stable [9] |
| 2-8° C. | 7d/4° C. [11] | 8d/4° C. (dark & in light) [5] <br> 7d/4° C. [11] | 14d/4° C. [8] <br> 7d/4° C. [7] <br> 2d/4° C. [9] |
| <0° C. | 28d /−20° C. [6] <br> 3m/−20° C. [1] <br> 3m/−20° C. [10] <br> 6m/−20° C. [11] <br> 8m/−20° C. [4] | 3m/−20° C. [1] <br> 6m/−20° C. [11] <br> 1a/−20 to −80° C. [3] | 7d/−20° C. [7] <br> 1m/−20° C. [9] <br> 1a/−70° C. [8] |

There is, thus, a need in the art for improved means and methods for determining immune-modulatory macrolides, in particular for improved means and methods for providing reliable and storable calibration solutions. This problem is solved by the means and methods disclosed herein.

Thus, the present invention relates to a liquid composition comprising at least one immune-modulatory macrolide and an essentially cell-free blood hemolysate.

DETAILED DESCRIPTION OF THE INVENTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value±20%, more preferably ±10%, most preferably, ±5%.

The term "liquid composition" is understood by the skilled person as opposed to solid or paste-like compositions. In an embodiment, the liquid composition is a Newtonian fluid. In a further embodiment, the liquid composition has a low viscosity, in an embodiment similar to water. Thus, in an embodiment, the viscosity of the liquid composition is less than 100 mPas, in an embodiment is less than 50 mPas, in a further embodiment less than 15 mPas. In an embodiment, viscosity is determined according to the Viscometer-Rheometer-on-a-Chip (VROC®) method (Sharma et al. (2011), Soft Matters 7:5150) at 20° C. In a further embodiment, viscosity determination is performed on a RheoSense m-VROC™ (Collotec) device at 20° C., in an embodiment according to instructions provided by the manufacturer. In an embodiment, the liquid composition is an aqueous composition, in an embodiment comprising water in a proportion of at least 50% (w/w), in an embodiment of at least 70% (w/w), in a further embodiment of at least 80% (w/w), in a further embodiment of at least 90% (w/w). In an embodiment, the liquid composition may comprise minor amounts of organic solvents, e.g. from the addition of a stock solution of an immune-modulatory macrolide. However, in an embodiment, the liquid composition comprises less than 10% organic solvent, in an embodiment less than 5% organic solvent, in a further embodiment less than 2% organic solvent, in a further embodiment less than 1% organic solvent. In an embodiment, the liquid composition is essentially free of detectable organic solvents, wherein the term "essentially free of" relates to a proportion of less than 0.1%, in a further embodiment relates to undetectable amounts. In an embodiment, the detection method used in such case is gas chromatography. In an embodiment, the liquid composition comprises everolimus, sirolimus, or tacrolimus, in an embodiment comprises everolimus and sirolimus, in an embodiment comprises sirolimus and tacrolimus, in an embodiment comprises everolimus and tacrolimus, in a further embodiment comprises everolimus, sirolimus, and tacrolimus. In an embodiment, the liquid composition is essentially cell free; thus, in an embodiment, the liquid composition comprises less than 10 viable cells/ml, in an embodiment less than 1 viable cell/ml. In a further embodiment, the liquid composition comprises less than 10 cells/ml, in an embodiment less than 1 cell/ml. In the context of a preparation being cell-free, the term "cell", in an embodiment, refers to eukaryotic cells, i.e., in particular, cells comprised in the preparation used for hemolysis. In an embodiment, the liquid composition has a pH of from 7.5 to 4, in a further embodiment of from 7 to 5. In an embodiment, in the liquid composition, the immune-modulatory macrolide(s) is/are stable for at least 12 months at a temperature of 6° C., the term "being stable" relating to a decrease in concentration of at most 10%, in an embodiment at most 5%, in a further embodiment within the standard deviation of the determination method.

In an embodiment, the liquid composition consists of at least one immune-modulatory macrolide and the essentially cell-free blood hemolysate. In a further embodiment, the liquid composition consists of at least one immune-modulatory macrolide, the essentially cell-free blood hemolysate, and one or more further immune-modulatory compounds. In a further embodiment, the liquid composition consists of at least one immune-modulatory macrolide, the essentially cell-free blood hemolysate, at least one preservative, and, optionally, one or more further immune-modulatory compounds.

In a further embodiment, the liquid composition is a calibration solution comprising a predetermined amount of the immune-modulatory macrolide or immune-modulatory macrolides, and, optionally, of at least one non-macrolide immune-modulatory compound. In an embodiment, the liquid composition comprises the immune-modulatory macrolide(s) at a concentration as specified elsewhere herein in such case, the indicated concentration ranges, in an embodiment, referring to the concentration of one specific immune-modulatory macrolide. As will be understood, accordingly, the total sum of immune-modulatory macrolides in the preparation may exceed the referenced concentration ranges. In an embodiment, the liquid composition is an immune-modulator calibration solution comprising a predetermined amount of an immune-modulatory macrolide, in an embodiment a predetermined amount of everolimus, sirolimus and/or tacrolimus. The liquid composition may also be a reference solution as specified elsewhere herein.

The term "macrolide", as used herein, relates a class of compounds comprising a macrocyclic lactone structure which are, in an embodiment, members of the polyketide class of compounds. In an embodiment, the macrocyclic lactone ring comprises of from 8 to 50 ring atoms, in an embodiment of from 12 to 40 ring atoms, in a further embodiment of from 15 to 35 ring atoms. In an embodiment, the macrolide comprises 23 ring atoms, such as in tacrolimus and in pimecrolimus, or the macrolide comprises 31 ring atoms, such as in sirolimus, everolimus, and temsirolimus. As is understood by the skilled person, the macrolide may comprise further ring structures directly or indirectly attached to the macrocyclic lactone ring, and/or the lactone ring and potential further rings may, in addition to the at least one oxygen heteroatom, comprise further heteroatoms, in particular nitrogen. Moreover, the macrolide may further comprise organic and/or inorganic side chains, including in particular methyl groups, ethyl groups, ethylene groups, keto groups, hydroxyl groups, cyclic alkyl groups, sugar residues, and the like.

The term "immune-modulatory macrolide", as used herein, relates to a macrolide as specified herein above having the property of modulating the immune response of a subject, in an embodiment of a mammal, in particular a human. In an embodiment, said modulation is a suppression; thus, in an embodiment, the immune-modulatory macrolide is an immune-suppressive compound of the macrolide class of compounds, i.e. is a macrolide immunosuppressant. In an embodiment, the immune-modulatory macrolide is a compound inhibiting T lymphocyte activation; means and methods for determining such activity are known to the skilled person. As will be understood by the skilled person, the immune-modulatory effect of an immune-modulatory macrolide may be direct, i.e. by the compound itself modulating an activity of a component of the immune system, or may indirect, e.g. by a metabolite of the immune-modulatory macrolide modulating an activity of a component of the immune system. In an embodiment, the immune-modulatory macrolide is comprised in the liquid composition at a concentration of from 1 ng/ml to 15 µg/ml, in an embodiment of from 5 ng/ml to 1 µg/ml, in a further embodiment of from 7.5 ng/ml to 500 ng/ml, in a further embodiment of from 10 ng/ml to 250 ng/ml.

In an embodiment, the immune-modulatory macrolide is:
everolimus ((1R,9S,12S,15R,16E,18R,19R,21R,23S,24E, 26E,28E,30S,32S,35R)-1,18-dihydroxy-12-[(2R)-1-[(1S, 3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo hexatriaconta-16, 24,26,28-tetraene-2,3,10,14,20-pentone, CAS-number 159351-69-6),
sirolimus ((1R,9S,12S,15R,16E,18R,19R,21R,23S,24E, 26E,28E,30S,32S,35R)-1,18-dihydroxy-12-{(2R)-1-[(1S, 3R,4R)-4-hydroxy-3-methoxycyclohexyl]-2-propanyl}-19,30-dimethoxy-15,17,21,23,29,35-hexamethyl-11,36-dioxa-4-azatricyclo hexatriaconta-16,24,26,28-tetraene-2,3,10,14,20-pentone, CAS number 53123-88-9,
tacrolimus ((1R,9S,12S,13R,14S,17R,18E,21S,23S,24R, 25S,27R)-1,14-dihydroxy-12-[(1E)-1-[(1R,3R,4R)-4-hydroxy-3-methoxycyclohexyl]prop-1-en-2-yl]-23,25-dimethoxy-13,19,21,27-tetramethyl-17-(prop-2-en-1-yl)-11,28-dioxa-4-azatricyclo octacos-18-ene-2,3,10,16-tetrone, CAS number 104987-11-3),
pimecrolimus ((1R,9S,12S,13R,14S,17R,18E,21S,23S,24R, 25S,27R)-12-[(1E)-1-[(1R,3R,4S)-4-chloro-3-methoxycyclohexyl]prop-1-en-2-yl]-17-ethyl-1,14-dihydroxy-23, 25-dimethoxy-13,19,21,27-tetramethyl-11,28-dioxa-4-azatricyclo octacos-18-ene-2,3,10,16-tetrone, CAS number 137071-32-0), or
temsirolimus ((1R,2R,4S)-4-[(2R)-2-[(1R,9S,12S,15R,16E, 18R,19R,21R,23S,24E,26E,28E,30S,32S,35R)-1,18-dihydroxy-19,30-dimethoxy-15,17,21,29,35-hexamethyl-2,3,10,14,20-pentaoxo-11,36-dioxa-4-azatricyclo hexatriaconta-16,24,26,28-tetraen-12-yl]propyl]-2-methoxycyclohexyl 3-hydroxy-2-(hydroxymethyl)-2-methylpropanoate, CAS number 162635-04-3).

In an embodiment, the immune-modulatory macrolide is at least one immune-modulatory macrolide selected from everolimus, sirolimus, tacrolimus, pimecrolimus and temsirolimus, in an embodiment is at least one immune-modulatory macrolide selected from everolimus, sirolimus, and tacrolimus, in a further embodiment comprises everolimus, in an embodiment comprises sirolimus, in an embodiment comprises tacrolimus.

The term "hemolysate", in accordance with the understanding of the skilled person, is used herein to relate to a preparation comprising lysed erythrocytes. Means and methods for lysing erythrocytes are known in the art an include in particular freezing and thawing of a preparation comprising erythrocytes, addition of ammonium-chloride or of a mixture of ammonium-chloride and potassium to a preparation comprising erythrocytes, or diluting a preparation comprising erythrocytes with a hypoosmolar diluent, e.g. with deionized or distilled water. In an embodiment, the hemolysate is obtained by applying an erythrocyte-lysing treatment to blood, i.e., in an embodiment, to whole blood. In an embodiment, the hemolysate is obtained by freezing and thawing a preparation of whole blood, which proceeding may, in an embodiment, be repeated. In a further embodiment, the blood hemolysate is obtained by freezing and thawing whole blood, in an embodiment a pool of whole blood from at least two, in an embodiment from at least five subjects. In an embodiment, the hemolysate is obtained according to the method of the present invention as specified herein below.

The hemolysate according to the present invention is essentially cell-free. As is understood by the skilled person, a hemolysate, in particular if obtained from whole blood, may still comprise a significant number of non-lysed erythrocytes, but also of other non-lysed cells, in particular lymphocytes. According to the present invention, in order to produce an essentially cell-free hemolysate, non-lysed cells are actively removed from the hemolysate by appropriate measures, including e.g. centrifugation, filtration, decanting, and the like. Such active steps removing non-lysed cells may, however, not always be fully effective. Thus, in an embodiment, the essentially cell-free blood hemolysate is a hemolysate comprising a number of less than 10 viable cells/ml, in an embodiment less than 1 viable cell/ml. In a further embodiment, the essentially cell-free blood hemolysate is a hemolysate comprising a number of less than 10 cells/ml, in an embodiment less than 1 cell/ml.

In an embodiment, the liquid composition further comprises at least one non-macrolide immune-modulatory compound, in an embodiment further comprises ciclosporin (cyclo-(L-Alanyl-D-alanyl-N-methyl-L-leucyl-N-methyl-L-leucyl-N-methyl-L-valyl-3-hydroxy-N,4-dimethyl-L-2-amino-6-octenoyl-L-a-amino-butyryl-N-methylglycyl-N-methyl-L-leucyl-L-valyl-N-methyl-L-leucyl); CAS number 59865-13-3).

It may be beneficial when storing a composition, in particular if long-term storage in a non-frozen state is envisaged, to include a preservative (preservative agent) that prevents microbial growth.

Thus, an aspect of the invention covers the need for effective preservation, e.g. for long term storage of the composition. Preservatives suitable to control bacterial and fungal growth and enabling long term storage and use of the composition are known, in principle, to the skilled person, e.g. from McDonnell and Russell (1999), Clin Microbiol Rev 12(1):147 and from EP 0 878 714 A1. Moreover, a number of preservatives and mixtures thereof are marketed under a variety of trade names. Thus, in an embodiment, the liquid composition further comprises at least one preservative, i.e. one or more preservatives. Suitable preservatives have no effect or no negative effect on the liquid composition, in particular on the immune-modulatory macrolide(s) comprised therein and on their stabilization. Thus, in an embodiment, preservatives having or releasing reactive groups (like e.g. aldehydes, halogen releasing agents, heavy metals, peroxygens, and ethylene oxide), preservatives belonging to the same or a similar class of chemical compounds as the immune-modulatory macrolides, e.g. macrolide antibiotics like erythromycin and polyketide-antibiotics like tetracycline, are avoided. In an embodiment, the preservative is a preservative not interfering with immune-modulatory macrolide determination. Thus, e.g. preservatives comprising or consisting of 3-Iodo-2-propynylbutyl-carbamate, 2-hydroxypyridin-N-oxide, 5-chloro-2-methyl-4-isothiazoline-3-one and/or 2-methyl-4-isothiazolin-3-one, o-Phenylphenol (alkaline or alcoholic, in an embodiment alcoholic), methylisothiazolon, azides, and bis-biguanides may be used. In an embodiment, the preservative is an azide, in a further embodiment sodium azide. In a further embodiment, the preservative is a bis-biguanide, in an embodiment is an anti-bacterial bis-biguanide, in a further embodiment is alexidine (1,1'-(1,6-Hexanediyl)bis{2-[N'-(2-ethylhexyl)carbamimidoyl]guanidine, CAS-number 22573-93-9) or chlorhexidine (N,N"-bis(4-chlorophenyl)-3,12-diimino-2,4,11,13-Tetraazatetradecanediimidamide, CAS number 55-56-1), in an embodiment is chlorhexidine.

In an embodiment, the preservative is present in the liquid composition at a concentration of from 0.005% (w/v) to 0.5% (w/v), in an embodiment of from 0.0075% (w/v) to 0.25% (w/v). In an embodiment, the preservative is sodium azide and is present at a concentration of from 0.005% (w/v) to 0.25% (w/v), in an embodiment of from 0.0075% (w/v) to 0.05% (w/v), in a further embodiment of about 0.009%. In a further embodiment, the preservative is a bis-biguanide, in an embodiment is alexidine and/or chlorhexidine and is present at a concentration of from 0.005% (w/v) to 0.5% (w/v), in an embodiment of from 0.01% (w/v) to 0.25% (w/v), in a further embodiment of about 0.25%.

In an embodiment, the liquid composition further comprises an anticoagulant. The term "anticoagulant" is, in principle, known to the skilled person. In an embodiment, the anticoagulant is a compound inhibiting at least one coagulation pathway, in an embodiment inhibiting both coagulation pathways (intrinsic and extrinsic). In an embodiment, the anticoagulant is a low molecular weight compound, in an embodiment with a molecular mass of less than 1000 Da, in an embodiment less than 500 Da. In an embodiment, the anticoagulant is a chelator of divalent cations, in an embodiment a calcium ion chelator. In an embodiment, the anticoagulant is citrate and/or ethylenediaminetetraacetic acid (2,2',2",2'''-(Ethane-1,2-diyldinitrilo)tetraacetic acid, EDTA). In an embodiment, the anticoagulant is an anticoagulant not degradable by microorganisms; in an embodiment, the anticoagulant is EDTA. Thus, in an embodiment, the hemolysate is produced from EDTA blood. Suitable concentrations of anticoagulants are known in the art; e.g. in case the anticoagulant is EDTA, the final concentration in the liquid composition, in an embodiment, is of from 0.01% (w/v) to 5% (w/v), in a further embodiment of from 0.02% (w/v) to 1% (w/v), in a further embodiment of from 0 025% (w/v) to 0.5% (w/v), in a further embodiment of about 0.1% (w/v).

Advantageously, it was found in the work underlying the present invention that solutions of immune-modulatory macrolides can be stabilized by the addition of a hemolysate. This way, the solutions which are usually rather unstable, can be stored without freezing for extended periods of time.

The definitions made above apply mutatis mutandis to the following. Additional definitions and explanations made further below also apply for all embodiments described in this specification mutatis mutandis. The present invention further relates to The present invention also relates to a method for manufacturing a stabilized immune-modulatory macrolide calibration solution, comprising a) preparing a solution comprising an essentially cell-free blood hemolysate, b) admixing a predetermined amount of at least one immune-modulatory macrolide into said solution comprising an essentially cell-free blood hemolysate, and, thereby c) manufacturing a stabilized immune-modulatory macrolide calibration solution.

The method of the present invention, for the avoidance of doubt, is an in vitro method. Moreover, it may comprise steps in addition to those explicitly mentioned above. For example, further steps may relate, e.g., to providing one or more blood samples for hemolysis for step a), or addition of further compounds, in particular one or more preservative(s) before or after step b). Moreover, one or more of said steps may be performed by automated equipment. As the skilled person will understand, the method described herein can also be used to manufacture a stabilized immune-modulatory macrolide reference solution.

In an embodiment, the solution comprising an essentially cell-free blood hemolysate of step a) consists of said essentially cell-free blood hemolysate. In a further embodiment, the solution comprising an essentially cell-free blood hemolysate is prepared from EDTA whole blood, e.g. from a pool of whole blood samples from one or more, in an embodiment apparently healthy, subjects. Thus, in an embodiment, the method comprises obtaining a pool of whole blood samples from at least two, in an embodiment at least five non-identical subjects, in an embodiment, humans.

Methods for hemolysing erythrocytes are specified herein above. In an embodiment, preparing a solution comprising an essentially cell-free blood hemolysate comprises freezing and thawing a liquid comprising erythrocytes, in particular whole blood, thereby providing a blood hemolysate. In an embodiment such freezing is freezing at a temperature of from −1° C. to −190° C., in an embodiment of from −10° C. to −100° C., in a further embodiment of from −50° C. to −90° C., in a further embodiment of about −80° C., in a further embodiment of −80° C. As is known to the skilled person, freezing may be performed in air at the indicated temperature, e.g. by placing sample into a freezer; however, freezing may be accelerated by known methods, including freezing in dry ice or in a dry ice/alcohol bath, in liquid air, and the like. In a further embodiment, thawing is thawing at a temperature of from 0° C. to 50° C., in an embodiment of from 4° C. to 45° C., in a further embodiment of from 10° C. to 40° C., in a further embodiment of from 20° C. to 30° C., in a further embodiment of about 25° C., in a further embodiment of 25° C. As is known to the skilled person, thawing may be performed in air at the indicated temperature; however, thawing may be accelerated by known methods, including thawing in a water bath, in a thermoblock, and the like. In an embodiment, thawing is thawing in air.

In an embodiment preparing a solution comprising an essentially cell-free blood hemolysate comprises stirring a hemolysate, in particular a blood hemolysate, in an embodiment obtained as specified above, for at least 5 min, in an embodiment for at least 10 min, in a further embodiment for at least 20 min. In an embodiment, the method comprises stirring a blood hemolysate for of from 5 min to 600 min, in an embodiment of from 100 min to 300 min, in an embodiment of from 15 min to 180 min, in a further embodiment of from 20 min to 120 min, in a further embodiment of from 30 min to 90 min, in a further embodiment about 60 min, in a further embodiment for 60 min.

As specified herein above, the liquid composition of the present invention comprises a hemolysate which is essentially cell-free. Thus, in the method of the present invention, in an embodiment, cells are removed from the crude hemolysate according to known methods, in particular as described herein above. In an embodiment, cells are removed by centrifuging the crude hemolysate. In an embodiment, centrifugation is further applied to remove other undesirable constituent of the crude hemolysate, e.g. precipitated proteins. The skilled person knows how to adjust centrifugation conditions accordingly. Thus, in an embodiment, centrifuging is performed at of from 500 g to 25000 g, in an embodiment of from 1000 g to 20000 g, in a further embodiment of from 5000 g to 15000 g, in a further embodiment of from 10000 g to 14000 g; in an embodiment, the aforesaid centrifugation is performed for at least 2 min, in an embodiment at least 5 min, in a further embodiment at least 15 min. In an embodiment, said centrifugation is performed for of from 2 min to 60 min, in an embodiment of from 5 min to 30 min, in a further embodiment of from 10 min to 20 min, in a further embodiment of about 15 min. In an embodiment, the method further comprises admixing a predetermined amount of at least one immune-modulatory macrolide into the supernatant of the centrifuged blood hemolysate.

As specified herein above, the liquid composition may further comprise a preservative. Thus, in an embodiment, the method further comprises a step of admixing a preservative, in an embodiment a preservative as specified herein above, in a further embodiment a bis-biguanide, in a further embodiment an antibacterial bis-biguanide to said solution comprising an essentially cell-free blood hemolysate. Said step of step of admixing a preservative may be performed before, simultaneously, or after admixing the at least one immune-modulatory macrolide. In an embodiment, the step of admixing a preservative may even be performed before hemolysis.

The present invention further relates to a kit comprising a liquid composition according to present invention and an immune-modulator detection agent.

The term "kit", as used herein, refers to a collection of the aforementioned compounds, means or reagents of the present invention which may or may not be packaged together. The components of the kit may be comprised by separate housings (i.e. as a kit of separate parts), or two or more components may be provided in a single housing. Moreover, it is to be understood that the kit of the present invention, in an embodiment, is to be used for practicing the method for determining an immune-modulatory macrolide compound referred to herein below. It is, in an embodiment, envisaged that components are provided in a ready-to-use manner for practicing the methods referred to herein. In an embodiment, all or some of said compounds are provided in concentrated liquid form wherein the concentrated component is diluted using a liquid such as an aqueous buffered solution or a solution comprising a hemolysate as specified elsewhere herein. Further, the kit, in an embodiment, contains instructions for carrying out said methods. The instructions can be provided by a user's manual in paper- or electronic form. In addition, the manual may comprise instructions for interpreting the results obtained when carrying out the aforementioned methods using the kit of the present invention. In an embodiment, the kit further comprises water, a buffer, and/or suitable containers for performing the method.

The term "detection agent", as used herein, relates to any agent assisting in detection of an immune-modulator, in an embodiment an immune-modulatory macrolide. Thus, the detection agent may be a lysis buffer, a release agent releasing at least one immune-modulatory macrolide from a sample, a protein-precipitating agent (such as, e.g. acetonitrile, or any other suitable organic solvent), one or more liquid chromatography buffer(s), an ion pair generating agent for mass spectrometry, or the like. In an embodiment, the detection agent is a chemical molecule binding, directly or indirectly, to the immune-modulatory macrolide of the present invention as specified herein above. As will be understood by the skilled person, the detection agent may also be an indirect detector compound, i.e. a detection agent not contacting the immune-modulatory macrolide directly, but by means of a further compound which itself binds to the immune-modulatory macrolide. In an embodiment, the detection agent is a direct detection agent, i.e. is an agent directly binding to the immune-modulatory macrolide. In an embodiment, the detection agent is an antibody, in an embodiment is an IgG. In an embodiment, the detection agent is a monoclonal antibody. In a further embodiment, the detection agent is an antibody bound to an indicator compound, i.e. to a compound whose presence in a sample can be detected by means known to the skilled person. Known indicator compounds include dyes, electrochemically active groups, or beads like latex beads.

The term "sample", as used herein, refers to any composition of matter suspected or known to comprise at least one immune-modulatory macrolide. In an embodiment, the sample is a sample of a subject, in an embodiment of a patient; in an embodiment, the sample is an isolated sample from a subject. Thus, in an embodiment, a sample is a sample of a body fluid, in an embodiment, blood, plasma, serum, saliva or urine, or a sample derived by lavage from tissues or organs, e.g. from the respiratory tract. In a further embodiment, the sample is a blood, plasma, serum or urine sample. In a further embodiment, the sample is a blood or plasma sample or is a serum or plasma sample, in a further embodiment is a blood sample. In an embodiment, in case the sample is a blood sample, the method of the present invention comprises a further step of obtaining a serum or plasma sample from said blood sample, comprises treating said sample with a release agent, or comprises hemolysing said sample. In an embodiment, the sample is a citrate blood sample, a heparin blood sample, or an EDTA blood sample. In a further embodiment, the sample is an EDTA blood sample. Biological samples can be derived from a subject as specified elsewhere herein. Techniques for obtaining the aforementioned different types of biological samples are well known in the art. For example, blood samples may be obtained by blood taking, e.g. by puncturing an arterial and/or a venous blood vessel. In an embodiment, the sample is a sample of cells, tissue, or an organ obtained from a subject. In an embodiment, in case said organ is live-critical, said subject is not a human. Such samples can be obtained by well-known techniques including, in an embodiment, scrapes, swabs or biopsies appropriate regions of a body. As is known to the skilled person, such samples can be obtained by use of brushes, (cotton) swabs, spatulae, rinse/wash fluids, punch biopsy devices, puncture of cavities with needles or surgical instrumentation.

The aforementioned samples are, in an embodiment, pre-treated before they are used for the method of the present invention. Said pre-treatment may include treatments required to release or separate the compounds comprised in the sample or to remove excessive material or waste.

Suitable techniques comprise centrifugation, extraction, fractioning, ultrafiltration, protein precipitation followed by filtration and purification and/or enrichment of compounds. As indicated herein above, pre-treatment may, e.g. be treating a blood sample with a release agent. Moreover, other pre-treatments may be carried out in order to provide the compounds in a form or concentration suitable for analysis. Pre-treated samples as described before are also comprised by the term "sample" as used in accordance with the present invention.

The term "subject", as used herein, relates to an animal, in an embodiment a mammal, in a further embodiment a primate, in a further embodiment a human. In an embodiment, the subject is an experimental animal, in particular a mouse, rat, guinea pig, pig, or dog. In a further embodiment, the subject is a livestock or companion animal, in particular a cat, dog, goat, sheep, cattle, horse, or pig. In an embodiment, the subject is a subject known or suspected to be treated with at least one immune-modulatory compound, in particular at least one immune-modulatory macrolide. Thus, in an embodiment, the subject is a transplant recipient, in particular a human transplant recipient under immunesuppressive treatment, in particular under immune-modulatory macrolide treatment.

The present invention further relates to a use of a solution comprising an essentially cell-free blood hemolysate and optionally a preservative for stabilizing at least one immune-modulatory macrolide, in an embodiment for stabilizing an immune-modulator calibration solution, in a further embodiment an immune-modulator calibration solution comprising at least one immune-modulatory macrolide. In an embodiment, the solution comprising an essentially cell-free blood hemolysate is a solution comprising an essentially cell-free blood hemolysate as described elsewhere herein, and/or is a solution comprising an essentially cell-free blood hemolysate prepared according to the method according to the present invention.

Further, the present invention relates to a device comprising the composition according to the present invention and/or the kit according to the present invention.

In an embodiment, the device is a drug monitoring device. The device may further comprise an analysis unit configured to determine the amount of at least one immune-modulatory macrolide in a sample of a subject. The device may further comprise an evaluation unit configured to calculate the amount of at least one immune-modulatory macrolide in a sample of a subject, in an embodiment based on the data obtained by the analysis unit. In a further embodiment, the device further comprises a refrigerating unit. In a further embodiment, the device further comprises an output unit operatively linked at least to the evaluation unit, which output unit may be e.g. a display unit and/or a printer.

The term "device", as used herein, relates to a system of means comprising at least the means described, operatively linked to each other as to allow the determination. How to link the means of the device in an operating manner will depend on the type of means included into the device. In an embodiment, the means are comprised by a single device. However, it is also contemplated that the means of the current invention, e.g. an analysis unit and an evaluation unit, in an embodiment, may appear as separate devices and are, in a further embodiment, packaged together as a kit. The person skilled in the art will realize how to link the means without further ado. Preferred devices are those which can be applied without the particular knowledge of a specialized technician. In an embodiment, the device is adapted to include an additional feature as described herein.

Furthermore, the present invention relates to a method for determining an immune-modulatory macrolide compound in a sample of a subject, comprising using at least one composition according to the present invention as a calibration sample and/or as a reference sample.

The method for determining an immune-modulatory macrolide compound is an in vitro method. Methods for determining an immune-modulatory macrolide compound in a sample are, in principle, known to the skilled person. According to the present invention, in an embodiment, the composition according to the present invention is used as a calibration sample, i.e. for the comparison of measurement values delivered by a device under test with those of a calibration standard of known accuracy. In a further embodiment, the composition according to the present invention is used as a reference sample, i.e. as a sample of known concentration for comparison of inter-laboratory results.

Moreover, the present invention relates to an immune-modulatory macrolide calibration solution comprising, in an embodiment consisting of, the liquid composition of the present invention.

In view of the above, the following embodiments are particularly envisaged:

1. A liquid composition comprising at least one immune-modulatory macrolide compound and an essentially cell-free blood hemolysate.

2. The liquid composition of embodiment 1, wherein essentially cell free is a number of less than 10 viable cells/ml, in an embodiment less than 1 viable cell/ml.

3. The liquid composition of embodiment 1 or 2, wherein essentially cell free is a number of less than 10 cells/ml, in an embodiment less than 1 cell/ml.

4. The liquid composition of any one of embodiments 1 to 3, wherein said liquid composition is essentially cell free.

5. The liquid composition of any one of embodiments 1 to 4, wherein said liquid composition is an aqueous solution.

6. The liquid composition of any one of embodiments 1 to 5, wherein said immune-modulatory macrolide is at least one immune-modulatory macrolide selected from everolimus, sirolimus, tacrolimus, pimecrolimus and temsirolimus, in an embodiment is at least one immune-modulatory macrolide selected from everolimus, sirolimus, and tacrolimus, in a further embodiment comprises everolimus, in an embodiment comprises sirolimus, in an embodiment comprises tacrolimus.

7. The liquid composition of any one of embodiments 1 to 6, wherein said liquid composition comprises everolimus and sirolimus, in an embodiment comprises sirolimus and tacrolimus, in an embodiment comprises everolimus and tacrolimus, in an embodiment comprises everolimus, sirolimus, and tacrolimus.

8. The liquid composition of any one of embodiments 1 to 7, wherein said liquid composition further comprises at least one non-macrolide immune-modulatory compound, in an embodiment further comprises ciclosporin (cyclo-(L-Alanyl-D-alanyl-N-methyl-L-leucyl-N-methyl-L-leucyl-N- methyl-L-valyl-3-hydroxy-N,4-dimethyl-L-2-amino-6-octenoyl-L-a-amino-butyryl-N-methylglycyl-N-methyl-L-leucyl-L-valyl-N-methyl-L-leucyl); CAS number 59865-13-3).

9. The liquid composition of any one of embodiments 1 to 8, wherein said liquid composition further comprises a preservative, in an embodiment a preservative not interfering with immune-modulatory macrolide determination.

10. The liquid composition of embodiment 9, wherein the concentration of said preservative is of from 0.005% (w/v) to 0.5% (w/v), preferably 0.0075% (w/v) to 0.25% (w/v).

11. The liquid composition of embodiment 9 or 10, wherein said preservative is at least one preservative selected from 3-Iodo-2-propynylbutylcarbamate, 2-hydroxypyridin-N-oxide, 5-chloro-2-methyl-4-isothiazoline-3-one and/or 2-methyl-4-isothiazolin-3-one, o-Phenylphenol (alkaline or alcoholic), methylisothiazolon, an azide, and a bis-biguanide, in an embodiment is a bis-biguanide.

12. The liquid composition of any one of embodiments 1 to 11, wherein said liquid composition further comprises an antibacterial bis-biguanide.

13. The liquid composition of embodiment 12, wherein said bis-biguanide is alexidine (1,1'-(1,6-Hexanediyl)bis{2-[N'-(2-ethylhexyl)carbamimidoyl]guanidine, CAS-number 22573-93-9) or chlorhexidine (N,N''-bis(4-chlorophenyl)-3,12-diimino-2,4,11,13-Tetraazatetradecanediimidamide, CAS number 55-56-1), in an embodiment is chlorhexidine.

14. The liquid composition of any one of embodiments 1 to 13, wherein said liquid composition has a pH of from 7.5 to 4, in an embodiment of from 7 to 5.

15. The liquid composition of any one of embodiments 1 to 14, wherein said liquid composition comprises less than 10% organic solvent, in an embodiment less than 5% organic solvent, in a further embodiment less than 2% organic solvent, in a further embodiment less than 1% organic solvent.

16. The liquid composition of any one of embodiments 1 to 15, wherein said liquid composition is essentially free of detectable organic solvents.

17. The liquid composition of any one of embodiments 1 to 16, wherein said immune-modulatory macrolide is comprised in said liquid composition at a concentration of from 1 ng/ml to 15 μg/ml, in an embodiment of from 5 ng/ml to 1 μg/ml, in a further embodiment of from 7.5 ng/ml to 500 ng/ml, in a further embodiment of from 10 ng/ml to 250 ng/ml.

18. The liquid composition of any one of embodiments 10 to 17, wherein said bis-biguanide, in an embodiment said antibacterial bis-biguanide, is present in said composition at a concentration of from 0.005% (w/v) to 0.5% (w/v), in an embodiment of from 0.01% (w/v) to 0.25% (w/v), in a further embodiment of about 0.25%.

19. The liquid composition of any one of embodiments 1 to 18, wherein said essentially cell-free blood hemolysate is obtained by freezing and thawing whole blood, in an embodiment a pool of whole blood from at least two, in an embodiment from at least five subjects.

20. The liquid composition of any one of embodiments 1 to 19, wherein said essentially cell-free blood hemolysate is obtained according to the method according to any one of embodiments of 28 to 43.

21. The liquid composition of any one of embodiments 1 to 20, wherein said liquid composition consists of said immune-modulatory macrolide and said essentially cell-free blood hemolysate.

22. The liquid composition of any one of embodiments 8 to 20, wherein said liquid composition consists of said immune-modulatory macrolide, said essentially cell-free blood hemolysate, and one or more further immune-modulatory compounds.

23. The liquid composition of any one of embodiments 9 to 20, wherein said liquid composition consists of said immune-modulatory macrolide, said essentially cell-free blood hemolysate, said preservative, and, optionally, one or more further immune-modulatory compounds.

24. The liquid composition of any one of embodiments 1 to 23, wherein said liquid composition is a calibration solution comprising a predetermined amount of said immune-modulatory macrolide or immune-modulatory macrolides, and, optionally, of said at least one non-macrolide immune-modulatory compound.

25. The liquid composition of any one of embodiments 1 to 24, wherein said liquid composition is an immune-modulator calibration solution comprising a predetermined amount of an immune-modulatory macrolide, in an embodiment a predetermined amount of everolimus, sirolimus and/or tacrolimus.

26. The liquid composition of any one of embodiments 1 to 25, wherein in said liquid composition, said immune-modulatory macrolide is stable for at least 12 months at a temperature of 6° C.

27. The liquid composition of embodiment 26, wherein being stable relates to a decrease in concentration of at most 10%, in an embodiment at most 5%, in a further embodiment within the standard deviation of the determination method.

28. A method for manufacturing a stabilized immune-modulatory macrolide calibration solution, comprising
 a) preparing a solution comprising an essentially cell-free blood hemolysate;
 b) admixing a predetermined amount of at least one immune-modulatory macrolide into said solution comprising an essentially cell-free blood hemolysate, and, thereby
 c) manufacturing a stabilized immune-modulatory macrolide calibration solution.

29. The method of embodiment 28, wherein said solution comprising an essentially cell-free blood hemolysate consists of said essentially cell-free blood hemolysate.

30. The method of embodiment 28 or 29, wherein said solution comprising an essentially cell-free blood hemolysate comprises an anticoagulant, in an embodiment comprises EDTA, in a further embodiment is prepared from EDTA whole blood.

31. The method of any one of embodiments 28 to 30, wherein said preparing a solution comprising an essentially cell-free blood hemolysate comprises freezing and thawing said whole blood, thereby providing a blood hemolysate.

32. The method of embodiment 31, wherein said freezing is freezing at a temperature of from −1° C. to −190° C., in an embodiment of from −10° C. to −100° C., in a further embodiment of from −50° C. to −90° C., in a further embodiment of about −80° C., in a further embodiment of −80° C.

33. The method of embodiment 31 or 32, wherein said thawing is thawing at a temperature of from 0° C. to 50° C., in an embodiment of from 4° C. to 45° C., in a further embodiment of from 10° C. to 40° C., in a further embodiment of from 20° C. to 30° C., in a further embodiment of about 25° C., in a further embodiment of 25° C.

34. The method of any one of embodiments 28 to 33, wherein said preparing a solution comprising an essentially cell-free blood hemolysate comprises stirring a blood hemolysate for at least 5 min, in an embodiment for at least 10 min, in a further embodiment for at least 20 min.

35. The method of any one of embodiments 28 to 34, wherein said preparing a solution comprising an essentially cell-free blood hemolysate comprises stirring a blood hemolysate for of from 5 min to 600 min, in an embodiment of from 100 min to 300 min, in an embodiment of from 15 min to 180 min, in a further embodiment of from 20 min to 120 min, in a further embodiment of from 30 min to 90 min, in a further embodiment about 60 min, in a further embodiment 60 min.

36. The method of any one of embodiments 28 to 35, wherein said preparing a solution comprising an essentially cell-free blood hemolysate comprises centrifuging a blood hemolysate.

37. The method of embodiment 36, wherein said centrifuging is performed at of from 500 g to 25000 g, in an embodiment of from 1000 g to 20000 g, in a further embodiment of from 5000 g to 15000 g, in a further embodiment of from 10000 g to 14000 g.

38. The method of embodiment 36 or 37, wherein said centrifugation is performed for at least 2 min, in an embodiment at least 5 min, in a further embodiment at least 15 min.

39. The method of any one of embodiments 36 to 38, wherein said centrifugation is performed for of from 2 min to 60 min, in an embodiment of from 5 min to 30 min, in a further embodiment of from 10 min to 20 min, in a further embodiment of about 15 min.

40. The method of any one of embodiments 28 to 39, wherein step b) comprises admixing said predetermined amount of at least one immune-modulatory macrolide into the supernatant of the centrifuged blood hemolysate.

41. The method of any one of embodiments 28 to 34, wherein said preparing a solution comprising an essentially cell-free blood hemolysate comprises obtaining a pool of whole blood samples from at least two, in an embodiment at least five non-identical subjects, in an embodiment, humans.

42. The method of any one of embodiments 28 to 41, wherein said method further comprises a step of admixing a preservative, in an embodiment a bis-biguanide, in a further embodiment an antibacterial bis-biguanide to said solution comprising an essentially cell-free blood hemolysate.

43. The method of embodiment 42, wherein said preservative is alexidine (1,1'-(1,6-Hexanediyl)bis{2-[N'-(2-ethylhexyl)carbamimidoyl]guanidine, CAS-number 22573-93-9) or chlorhexidine (N,N'''-bis(4-chlorophenyl)-3,12-diimino-2,4,11,13-Tetraazatetradecanediimidamide, CAS number 55-56-1), in an embodiment is chlorhexidine.

44. A kit comprising a liquid composition according to any one of embodiments 1 to 27 and an immune-modulator detection agent.

45. Use of a solution comprising an essentially cell-free blood hemolysate and optionally a preservative for stabilizing at least one immune-modulatory macrolide, in an embodiment for stabilizing an immune-modulator calibration solution, in a further embodiment an immune-modulator calibration solution comprising at least one immune-modulatory macrolide.

46. The use of embodiment 45, wherein said solution comprising an essentially cell-free blood hemolysate is a solution comprising an essentially cell-free blood hemolysate as described in any one of embodiments 1 to 4, and/or is a solution comprising an essentially cell-free blood hemolysate prepared according to the method according to any one of embodiment 28 to 42.

47. A device comprising the composition according to any one of embodiments 1 to 27 and/or the kit according to embodiment 44.

48. The device of embodiment 47, wherein said device is a drug monitoring device.

49. The device of embodiment 47 or 48, wherein said device further comprises an analysis unit configured to determine the amount of at least one immune-modulatory macrolide in a sample of a subject.

50. The device of any one of embodiments 47 to 49, wherein said device further comprises a refrigerating unit.

51. A method for determining an immune-modulatory macrolide compound in a sample of a subject, comprising using at least one composition according to any one of embodiments 1 to 27 as a calibration sample and/or as a reference sample.

52. An immune-modulatory macrolide compound calibration solution comprising, in an embodiment consisting of, the liquid composition of any one of embodiments 1 to 27.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Assessment of Everolimus Stability—Real-Time-Stability (RTS)

A formulation was prepared by firstly hemolyzing human whole blood: Human EDTA whole blood of 5 donors was hemolyzed by a freeze-and-thaw cycle. After freezing the whole blood sample from each donor separately at −80° C. and thawing at room temperature, all samples were combined, mixed on a roller for at least 1 hour and then centrifuged for 15 minutes at 22° C. and 12000 g in order to remove fragments of hemolyzed blood cells potentially present. After the centrifugation, the upper section (approximately ⅘ of the whole volume) of the hemolyzed blood was used as hemolysate. Finally, chlorhexidine was added to the hemolysate to a concentration of 0.024%.

For checking the RTS, the chlorhexidine-containing hemolysate was spiked from a highly concentrated stock solution of everolimus to approx. 100 ng/ml, and aliquots thereof were stressed at 6° C. for 3, 6, 9, 12, and 15 months respectively in brown LC-MS vials. The stressed samples and the corresponding non-stressed samples (T0 samples) were analyzed by LC-MS/MS measurements.

LC-MS/MS method: Before performing the LC-MS/MS analysis, the samples were treated by addition of 10 µL isotope-labeled internal standards (d4/2×C13—everolimus) to 100 µL of the sample to be analyzed, followed by a protein precipitation by addition of 150 µL acetonitrile. The mixture was incubated at 4° C. for 60 minutes and then centrifuged (18000 g, 4° C., 30 min). The supernatant was diluted 1:4 with a solvent mixture of 30% acetonitrile and 70% water and then injected in the LC-MS/MS. The samples were quantified by an external calibration curve. The calibrator was a set of solutions with different concentrations of analyte and they were run through the same preparation workflow, with the same internal standard as the samples. For the calculation of the concentration in a sample, the response factors (ratio of analyte peak area and internal standard peak area) of the sample were referenced with the linear function of the calibration curve (ratio by concentration). The recovery value was the concentration measured at time point (Ti) compared to the non-stressed concentration at start time point (T0) as reference (see Table 3). Formulations with recoveries >90% were classified as stable.

LC-MS/MS conditions were
Solvents: A: 0.5 mM NH₄Acetate in H₂O/B: Methanol
Gradient: according to Table 2.
AB Sciex 6500 QTRAP/Agilent HPLC 1290-Infinity
APCI source negative mode
Column: Phenomenex—Kinetex F5, 2.6 µm particle, 150 mm×2.1 mm
Temperature: 50° C. (Column) and 8° C. (Autosampler)
Injection volume 20 µL
Calibration: external, with 6 concentration levels covering 0-500 ng/mL
MRM Transition at DP: −76 V EP: −10 V CE: −30 V CXP: −24 V
Detection: everolimus: Q1: 956.6 Da Q3: 590.2 Da; everolimus d4,2×C13: Q1: 962.2 Da Q3: 590.2 Da.

Table 2: LC gradient:

|   | Time [min] | Flow Rate [µl/min] | A % | B % |
|---|---|---|---|---|
| 1 | 0.0 | 350 | 30 | 70 |
| 2 | 6.0 | 350 | 12 | 88 |
| 3 | 6.25 | 350 | 0 | 100 |
| 4 | 9.0 | 350 | 0 | 100 |
| 5 | 9.25 | 350 | 30 | 70 |
| 6 | 12.0 | 350 | 30 | 70 |

For checking the isotope stability of the isotope-labelled everolimus (d4/2×C13), the compound was stressed together with equimolar amount of non-isotope labeled everolimus as internal standard. After preparation workflow and measurement by LC-MS/MS, the resulting ratio should be around 1 in case that the isotope-labeled compound is stable, and the obtained value is without unit. The recovery value is the ratio determined at time point (Ti) compared to the non-stressed ratio at start time point (T0) as reference (see Table 3). This experiment is just referencing the stability of the isotope-label and not the stability of the compound. For statements of compound stability, just the previous described experiment is suitable.

Results: A real-time stability of 15 months could be successfully demonstrated for Eve in the described formulation. The data for the recoveries after 3, 6, 9, 12, and 15 months are shown in the table below. Also the data (12 months) for the isotope-labeled compound indicate that the isotope-labeled Eve is stable.

Table 3: Recovery values for stressed everolimus and d4/2×C13—everolimus at 6° C.

|   | T0 | 3 months | 6 months | 9 months | 12 months | 15 months |
|---|---|---|---|---|---|---|
| Eve | 74.8 ng/mL | 71.1 ng/mL | 81.8 ng/mL | 74.6 ng/mL | 92.0 ng/mL | 77.8 ng/mL |
|  | 100% | 95% | 109% | 100% | 123% | 104% |
| d4/2×C13 Eve | 0.946 | 0.955 | 0.931 | 0.952 | 0.955 | n.d. |
|  | 100% | 101% | 98% | 101% | 101% | n.d. |

Example 2: Assessment of Sirolimus and Tacrotimus Stability—Real-Time-Stability (RTS)

A formulation was prepared by firstly hemolyzing human whole blood: Human EDTA whole blood of 5 donors was hemolyzed by a freeze-and-thaw cycle. After freezing the whole blood sample from each donor separately at −80° C. and thawing at room temperature, all samples were combined, mixed on a roller for at least 1 hour and then centrifuged for 15 minutes at 22° C. and 12000 g in order to remove fragments of hemolyzed blood cells potentially present. After the centrifugation, the upper section (approximately ⅘ of the whole volume) of the hemolyzed blood was used as hemolysate. Finally, chlorhexidine was added to the hemolysate to a concentration of 0.024%.

For checking the RTS, the chlorhexidine-containing hemolysate was spiked from a highly concentrated stock solution of sirolimus to approx. 100 ng/mL or tacrolimus to approx. 135 ng/mL, and aliquots thereof were stressed at 6° C. for 3 months respectively in brown LC-MS vials. The stressed samples and the corresponding non-stressed samples (T0 samples) were stored at 6° C. for a couple of days until their LC-MS/MS analysis.

LC-MS/MS method: Before performing the LC-MS/MS analysis the samples were prepared by addition of 10 µL structurally similar internal standards (everolimus D4 2×C13 for sirolimus and non-labeled ascomycin for tacrolimus) to 100 µL of the sample to be analyzed, followed by a protein precipitation by addition of 150 µL acetonitrile. The mixture was incubated at 4° C. for 60 minutes and then centrifuged (18000 g, 4° C., 30 min). The supernatant was 1:4 diluted with a solvent mixture of 30% acetonitrile and 70% deionized water and then injected in the LC-MS/MS. The recovery value was the found area-ratio at time point ($T_1$) compared to the non-stressed area-ratio at start time point ($T_0$) as reference (see table 5). Formulations with recoveries >90% were classified as stable and with 80-90% as acceptable.

LC-MS/MS conditions were
Solvents: A: 5 mM NH₄Acetate in H₂O+0.1% Formic acid/
B: Methanol+0.1% Formic acid
Gradient: according to Table 4.
AB Sciex Triple Quad 6500+/Agilent HPLC 1290-Infinity II
ESI source
Column: Phenomenex—Kinetex F5, 2.6 µm particle, 50 mm×2.1 mm
Temperature: 40° C. (Column) and 8° C. (Autosampler)
Injection volume 20 µL
MRM Transition at DP: 70 V EP: 10 V CXP: 12 V
Detection: everolimus: Q1: 975.7 Da Q3: 908.7 Da CE 25 V
   everolimus d4,2×C13: Q1: 981.7 Da Q3: 914.7 Da CE 25 V
   sirolimus: Q1: 931.7 Da Q3: 864.6 Da CE 25 V
   tacrolimus: Q1: 821.5 Da Q3: 576.4 Da CE 33 V
   ascomycin: Q1: 809.5 Da Q3: 564.4 Da CE 33 V Table 4: LC gradient:

|   | Time [min] | Flow Rate [µl/min'] | A % | B % |
|---|---|---|---|---|
| 1 | 0.0 | 600 | 50 | 50 |
| 2 | 2.0 | 600 | 0 | 100 |
| 3 | 3.0 | 600 | 0 | 100 |

-continued

| Time [min] | Flow Rate [µl/min'] | A % | B % |
|---|---|---|---|
| 4 | 3.2 | 600 | 50 | 50 |
| 5 | 4.5 | 600 | 50 | 50 |

Results: A real-time stability of 3 months could be successfully demonstrated for sirolimus and tacrolimus in the described formulation. The data for the recoveries after 3 months are shown in Table 5 below.

Table 5: Recovery values for stressed non-labeled sirolimus and tacrolimus at 6° C.

|  | T0 | 3 months |
|---|---|---|
| sirolimus | 0.745 | 0.606 |
|  | 100% | 81% |
| tacrolimus | 0.99 | 0.972 |
|  | 100% | 98% |

Example 3: Real-Time-Stability Study

In a short 3-month real-time-stability study it was also checked if NaN3 could be applied as conservation additive. The procedure was as described above in Example 1, however, with the addition of 0.009% sodium azide instead of chlorhexidine. The results, shown in Table 6, indicate also here a stable formulation.

Table 6: Recovery values for stressed everolimus at 6° C. with NaN3 as additive

|  | T0 | 3 months |
|---|---|---|
| everolimus | 0.781 | 0.732 |
|  | 100% | 94% |

The invention claimed is:

1. A liquid composition comprising at least one immune-modulatory macrolide compound and an essentially cell-free blood hemolysate, wherein said immune-modulatory macrolide is at least one immune-modulatory macrolide selected from the group consisting of everolimus, sirolimus, tacrolimus, pimecrolimus and temsirolimus, and wherein essentially cell free is a number of less than 10 viable cells/ml.

2. The liquid composition of claim 1, wherein essentially cell free is a number of less than 1 viable cell/ml.

3. The liquid composition of claim 1, wherein said liquid composition is an aqueous solution.

4. The liquid composition of claim 1, wherein said immune-modulatory macrolide is at least one immune-modulatory macrolide selected from the group consisting of everolimus, sirolimus and tacrolimus.

5. The liquid composition of claim 1, wherein said liquid composition further comprises a preservative.

6. The liquid composition of claim 5, wherein said preservative is alexidine.

7. The liquid composition of claim 1, wherein said liquid composition has a pH of from 7.5 to 4.

8. A method for manufacturing a stabilized immune-modulatory macrolide calibration solution, comprising
a) preparing a solution comprising an essentially cell-free blood hemolysate,
b) admixing a predetermined amount of at least one immune-modulatory macrolide into said solution comprising an essentially cell-free blood hemolysate, and, thereby
c) manufacturing a stabilized immune-modulatory macrolide calibration solution,
wherein said immune-modulatory macrolide is at least one immune-modulatory macrolide selected from the group consisting of everolimus, sirolimus, tacrolimus, pimecrolimus and temsirolimus, and wherein essentially cell free is a number of less than 10 viable cells/ml.

9. The method of claim 8, wherein said preparing a solution comprising an essentially cell-free blood hemolysate comprises freezing and thawing whole blood, thereby providing a blood hemolysate; and/or wherein said preparing a solution comprising an essentially cell-free blood hemolysate comprises stirring said blood hemolysate for at least 5 min.

10. The method of claim 9, wherein said preparing a solution comprising an essentially cell-free blood hemolysate comprises centrifuging said blood hemolysate.

11. A kit comprising a liquid composition according to claim 1 and an immune-modulator detection agent.

12. The liquid composition of claim 5, wherein the preservative does not interfere with immune-modulatory macrolide determination.

13. The liquid composition of claim 5, wherein the preservative comprises a bis-biguanide.

* * * * *